United States Patent [19]

Vaccaro

[11] Patent Number: 5,688,785
[45] Date of Patent: Nov. 18, 1997

[54] SUBSTITUTED AZETIDINONE COMPOUNDS USEFUL AS HYPOCHOLESTEROLEMIC AGENTS

[75] Inventor: Wayne D. Vaccaro, Yardley, Pa.

[73] Assignee: Schering Corporation, Kenilworth, N.J.

[21] Appl. No.: 449,973

[22] Filed: May 25, 1995

Related U.S. Application Data

[63] Continuation-in-part of Ser. No. 261,785, Jun. 20, 1994, abandoned, which is a continuation-in-part of Ser. No. 178,312, filed as PCT/US92/05972 Jul. 21, 1992, abandoned, which is a continuation-in-part of Ser. No. 734,652, Jul. 23, 1991, abandoned, and Ser. No. 734,426, Jul. 23, 1991, abandoned.

[51] Int. Cl.$^6$ ............ C07D 205/08; A61K 31/395
[52] U.S. Cl. ............ 514/210; 540/200; 540/360
[58] Field of Search ............ 540/360, 200; 514/210

[56] References Cited

U.S. PATENT DOCUMENTS

| | | | |
|---|---|---|---|
| 4,166,907 | 9/1979 | Krapcho | 540/200 |
| 4,260,743 | 4/1981 | Bose | 540/364 |
| 4,834,846 | 5/1989 | Abramson | 540/200 |
| 4,983,597 | 1/1991 | Yang et al. | 514/210 |
| 5,030,628 | 7/1991 | Joyeau et al. | 514/210 |
| 5,306,817 | 4/1994 | Thiruvengadam | 540/200 |

FOREIGN PATENT DOCUMENTS

| | | |
|---|---|---|
| 199630 | 10/1986 | European Pat. Off. |
| 264231 | 4/1988 | European Pat. Off. |
| 337549 | 10/1989 | European Pat. Off. |
| 365364 | 4/1990 | European Pat. Off. |
| 375527 | 6/1990 | European Pat. Off. |
| 462667 | 12/1991 | European Pat. Off. |
| 481671 | 4/1992 | European Pat. Off. |
| WO 93/02048 | 2/1993 | WIPO. |
| 95/08532 | 3/1995 | WIPO. |

OTHER PUBLICATIONS

Ram et al., *Indian J. Chem.*, Sect. B, 29B, 12(1990), pp. 1134–1137.
Oppolzer et al, *Tet. Lett.*, 25 (1984), pp. 5885–5888.
Derwent Abstract of JP 61-057,580 (1984).
Derwent Abstract of JP 62-081,368 (1985).
Derwent Abstract of JP 61-280,295 (1984).
Derwent Abstract of JP 56-125,360 (1980).
Derwent Abstract of JP 56-061,352 (1980).
Harwood et al., *J. Lipid Research*, 34, (1993), pp. 377–395
*Atherosclerosis*, 115, (1995), pp. 45–63.
Schnitzer–Polokoff, et al. *Comp. Biochem. Physiol.*, 99A (1991), pp. 665–670.
Witzum, *Circulation*, 80, 5 (1989), pp. 1101–1114.
Illingworth, *Drugs*, 36(Supp. 3) (1988), pp. 63–71.
Allain, et al, *Clin. Chem.*, 20, (1974), pp. 470–475.
Horie, et al., *Atherosclerosis*, 88 (1991), pp. 183–192.

Baxter er al., *J. Biological Chem.*, 267, 17 (1992), pp. 11705–11708.
*Current Drugs: Anti–Atherosclerotic Agents*—Summary Factfile, May, 1992.
"Naming and Indexing of Chemical Substance for Chemical Abstracts" Appendix IV, p. 1031 (1982).

Primary Examiner—Mark L. Berch
Attorney, Agent, or Firm—Anita W. Magatti

[57] ABSTRACT

Substituted azetidinone hypocholesterolemic agents of the formula

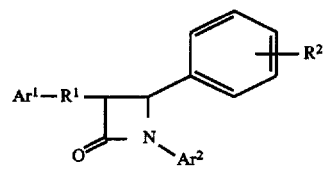

I or a pharmaceutically acceptable salt thereof, wherein:

$Ar^1$ is aryl or $R^3$-substituted aryl;

$Ar^2$ is aryl or $R^4$-substituted aryl;

$R^1$ is selected from the group consisting of
—$(CH_2)_q$—, wherein q is 2, 3, 4, 5 or 6;
—$(CH_2)_e$—Z—$(CH_2)_r$—, wherein Z is —O—, —C(O)—, phenylene, —$NR^{10}$— or —$S(O)_{0-2}$—, e is 0–5 and r is 0–5, provided that the sum of e and r is 1–6;
—$(C_2$—$C_6$ alkenylene)—; and
—$(CH_2)_f$—V—$(CH_2)_g$—, wherein V is $C_3$–$C_6$ cycloalkylene, f is 1–5 and g is 0–5, provided that the sum of f and g is 1–6;

$R^2$ is —(lower alkylene)—$COR^5$ or —(CH=CH)—$COR^5$;

$R^3$ and $R^4$ are independently selected from the group consisting of 1–3 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —(lower alkylene)—$COOR^6$, —CH=CH—$COOR^6$, —$CF_3$, —CN, —$NO_2$ and halogen;

$R^5$ is —OR or —$NRR^{12}$, wherein R and $R^{12}$ are independently selected from the group consisting of hydrogen, lower alkyl, aryl and aryl-substituted lower alkyl;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is hydrogen, lower alkyl, aryl lower alkyl or —$C(O)R^6$.

are disclosed, as well as a method of lowering serum cholesterol by administering said compounds, alone or in combination with a cholesterol biosynthesis inhibitor, and pharmaceutical compositions containing them.

6 Claims, No Drawings

SUBSTITUTED AZETIDINONE COMPOUNDS USEFUL AS HYPOCHOLESTEROLEMIC AGENTS

This application is a continuation-in-part of U.S. Ser. No. 08/261,785, abandoned filed Jun. 20, 1994, which is a continuation-in-part of U.S. Ser. No. 178,312, filed Jan. 11, 1994, now abandoned, a § 371 of International Application No. PCT/US92/05972, filed Jul. 21, 1992, and designating the U.S., which PCT application in turn is a continuation-in-part of U.S. Ser. No. 734,652, filed Jul. 23, 1991, now abandoned and of U.S. Ser. No. 734,426, filed Jul. 23, 1991, now abandoned.

BACKGROUND OF THE INVENTION

The present invention relates to substituted azetidinones useful as hypocholesterolemic agents in the treatment and prevention of atherosclerosis, and to the combination of a substituted azetidinone of this invention and a cholesterol biosynthesis inhibitor for the treatment and prevention of atherosclerosis.

Atherosclerotic coronary heart disease (CHD) represents the major cause for death and cardiovascular morbidity in the western world. Risk factors for atherosclerotic coronary heart disease include hypertension, diabetes mellitus, family history, male gender, cigarette smoke and serum cholesterol. A total cholesterol level in excess of 225–250 mg/dl is associated with significant elevation of risk of CHD.

Cholesteryl esters are a major component of atherosclerotic lesions and the major storage form of cholesterol in arterial wall cells. Formation of cholesteryl esters is also a key step in the intestinal absorption of dietary cholesterol. Thus, inhibition of cholesteryl ester formation and reduction of serum cholesterol is likely to inhibit the progression of atherosclerotic lesion formation, decrease the accumulation of cholesteryl esters in the arterial wall, and block the intestinal absorption of cholesterol.

A few azetidinones have been reported as being useful in lowering cholesterol and/or in inhibiting the formation of cholesterol-containing lesions in mammalian arterial walls. U.S. Pat. No. 4,983,597 discloses N-sulfonyl-2-azetidinones as anticholesterolemic agents and Ram, et al., in *Indian J. Chem., Sect. B.* 29B, 12 (1990), p. 1134–7, disclose ethyl 4-(2-oxoazetidin-4-yl)phenoxy-alkanoates as hypolipidemic agents. European Patent Publication 264,231 discloses 1-substituted-4-phenyl-3-(2-oxoalkylidene)-2-azetidinones as blood platelet aggregation inhibitors. European Patent 199,630 and European Patent Application 337,549 disclose elastase inhibitory substituted azetidinones said to be useful in treating inflammatory conditions resulting in tissue destruction which are associated with various disease states, e.g. atherosclerosis.

WO93/02048, published Feb. 4, 1993, discloses substituted β-lactams useful as hypocholesterolemic agents.

The regulation of whole-body cholesterol homeostasis in humans and animals involves the regulation of dietary cholesterol and modulation of cholesterol biosynthesis, bile acid biosynthesis and the catabolism of the cholesterol-containing plasma lipoproteins. The liver is the major organ responsible for cholesterol biosynthesis and catabolism and for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When intestinal cholesterol absorption is reduced, by whatever means, less cholesterol is delivered to the liver. The consequence of this action is decreased hepatic lipoprotein (VLDL) production and an increase in the hepatic clearance of plasma cholesterol, mostly as LDL. Thus, the net effect of inhibiting intestinal cholesterol absorption is a decrease in plasma cholesterol levels.

The inhibition of cholesterol biosynthesis by 3-hydroxy-3-methylglutaryl coenzyme A (HMG CoA) reductase (EC1.1.1.34) inhibitors has been shown to be an effective way to reduce plasma cholesterol (Witzum, *Circulation*, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, *Drugs*, 36 (Suppl. 3) (1988), p. 63–71).

SUMMARY OF THE INVENTION

Novel hypocholesterolemic compounds of the present invention are represented by the formula I

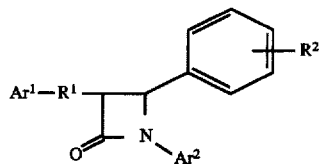

or a pharmaceutically acceptable salt thereof, wherein:

$Ar^1$ is aryl or $R^3$-substituted aryl;

$Ar^2$ is aryl or $R^4$-substituted aryl;

$R^1$ is selected from the group consisting of
—$(CH_2)_q$—, wherein q is 2, 3, 4, 5 or 6;
—$(CH_2)_e$—Z—$(CH_2)_r$—, wherein Z is —O—, —C(O)—, phenylene, —$NR^{10}$— or —$S(O)_{0-2}$—, e is 0–5 and r is 0–5, provided that the sum of e and r is 1–6;
—($C_2$-$C_6$ alkenylene)—; and
—$(CH_2)_f$—V—$(CH_2)_g$—, wherein V is $C_3$-$C_6$ cycloalkylene, f is 1–5 and g is 0–5, provided that the sum of f and g is 1–6;

$R^2$ is —(lower alkylene)—$COR^5$ or —(CH=CH)—$COR^5$;

$R^3$ and $R^4$ are independently selected from the group consisting of 1–3 substituents independently selected from the group consisting of lower alkyl, —$OR^6$, —O(CO) $R^6$, —O(CO) $OR^9$, —$O(CH_2)_{1-5}OR^6$, —O(CO)N $R^6R^7$, —$NR^6R^7$, —$NR^6(CO)R^7$, —$NR^6$ (CO)$OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —(lower alkylene)—$COOR^6$, —CH=CH—$COOR^6$, —$CF_3$, —CN, —$NO_2$ and halogen;

$R^5$ is —OR or —$NRR^{12}$, wherein R and $R^{12}$ are independently selected from the group consisting of hydrogen, lower alkyl, aryl and aryl-substituted lower alkyl;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is hydrogen, lower alkyl, aryl lower alkyl or —C(O) $R^6$.

Preferred are compounds of formula I wherein $Ar^1$ is phenyl or $R^3$-substituted phenyl, especially (4-$R^3$)- substituted phenyl. Also preferred are compounds of formula I wherein $Ar^2$ is phenyl or $R^4$-substituted phenyl, especially (4-$R^4$)-substituted phenyl.

$R^3$, when present, is preferably a halogen. $R^4$, when present, is preferably halogen or —$OR^6$, wherein $R^6$ is lower alkyl or hydrogen. Especially preferred are compounds wherein $Ar^2$ is 4-fluorophenyl.

$R^1$ is preferably —$(CH_2)_q$— or —$(CH_2)_e$—Z—$(CH_2)_r$—, wherein referred values for q are 2 and 3; Z is preferably —O—; e is preferably 0; and r is preferably 2.

$R^2$ is preferably in the para-position. When $R^2$ is —(lower alkylene)—$COOR^5$, the lower alkylene portion is preferably methylene or ethylene. $R^5$ is preferably lower alkyl, especially methyl, or hydrogen.

Another group of preferred compounds is that wherein $Ar^1$ is phenyl or $R^3$-substituted phenyl, especially (4-$R^3$)-substituted phenyl, $Ar^2$ is phenyl or $R^4$-substituted phenyl, especially (4-$R^4$)-substituted phenyl, and $R^1$ is —$(CH_2)_q$— or —$(CH_2)_e$—Z—$(CH_2)_r$—, wherein Z is —O—.

This invention also relates to a method of lowering the serum cholesterol level in a mammal in need of such treatment comprising administering an effective amount of a compound of formula I. That is, the use of a compound of the present invention as an hypocholesterolemic agent is also claimed.

In still another aspect, the present invention relates to a pharmaceutical composition comprising a serum cholesterol-lowering effective amount of a compound of formula I in a pharmaceutically acceptable carrier.

The present invention also relates to a method of reducing plasma cholesterol levels, and to a method of treating or preventing atherosclerosis, comprising administering to a mammal in need of such treatment an effective amount of a combination of a substituted azetidinone cholesterol absorption inhibitor of formula I and a cholesterol biosynthesis inhibitor. That is, the present invention relates to the use of a substituted azetidinone cholesterol absorption inhibitor of formula I for combined use with a cholesterol biosynthesis inhibitor (and, similarly, use of a cholesterol biosynthesis inhibitor for combined use with a substituted azetidinone cholesterol absorption inhibitor of formula I) to treat or prevent atherosclerosis or to reduce plasma cholesterol levels.

In yet another aspect, the invention relates to a pharmaceutical composition comprising an effective amount of a substituted azetidinone cholesterol absorption inhibitor of formula I, a cholesterol biosynthesis inhibitor, and a pharmaceutically acceptable carrier. In a final aspect, the invention relates to a kit comprising in one container an effective amount of a substituted azetidinone cholesterol absorption inhibitor of formula I in a pharmaceutically acceptable carrier, and in a separate container, an effective amount of a cholesterol biosynthesis inhibitor in a pharmaceutically acceptable carrier.

DETAILED DESCRIPTION

As used herein, the term "lower alkyl" means straight or branched alkyl chains of 1 to 6 carbon atoms. Similarly, "lower alkylene" means a divalent alkyl chain, straight or branched, of 1 to 6 carbon atoms, and "cycloalkylene" means a divalent cycloalkyl group.

"Aryl" means phenyl, naphthyl, indenyl, tetrahydronaphthyl or indanyl. "Phenylene" means a divalent phenyl group.

"Halogeno" refers to fluorine, chlorine, bromine or iodine atoms.

Compounds of the invention have at least one asymmetric carbon atom and therefore all isomers, including enantiomers and diastereomers are contemplated as being part of this invention. The invention includes d and l isomers in both pure form and in admixture, including racemic mixtures. Isomers can be prepared using conventional techniques, either by reacting chiral starting materials or by separating isomers of a compound of formula I. Isomers may also include geometric isomers, e.g. when a double bond is present. All such geometric isomers are contemplated for this invention.

Those skilled in the art will appreciate that for some compounds of formula I, one isomer will show greater pharmacological activity than another isomer.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base form for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination of the present invention include HMG CoA reductase inhibitors such as lovastatin, pravastatin, fluvastatin, simvastatin, and CI-981; HMG CoA synthetase inhibitors, for example L-659,699 ((E,E)-11-[3'R-(hydroxymethyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride) and other cholesterol biosynthesis inhibitors such as DMP-565. Preferred HMG CoA reductase inhibitors are lovastatin, pravastatin and simvastatin.

Compounds of formula I can be prepared by known methods, for example those described in WO93/02048 cited above. Following are general schematic representations of typical procedures; the examples below provide more detailed descriptions. Most of the abbreviations are defined in the examples below; those that are not include Pd(OAc)$_2$ (palladium diacetate); Ph$_3$P (triphenylphosphine); Tf$_2$O (triflic anhydride).

Method A:

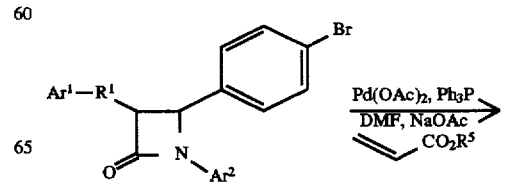

5
-continued
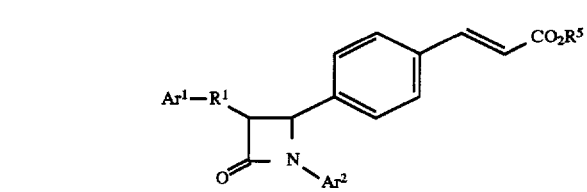
Method B:
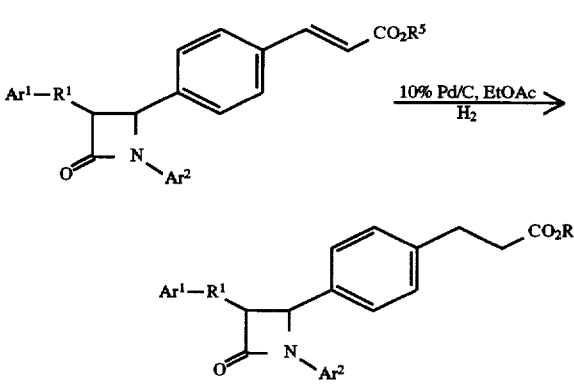
Method C:
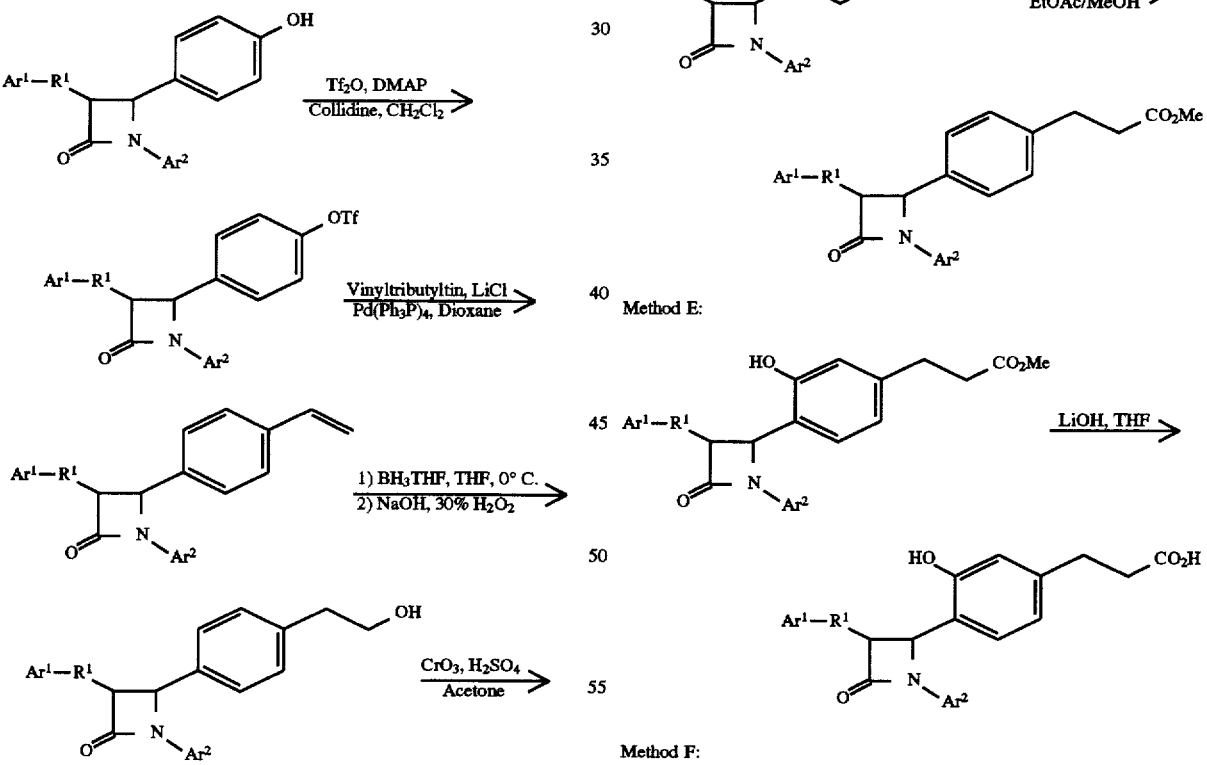
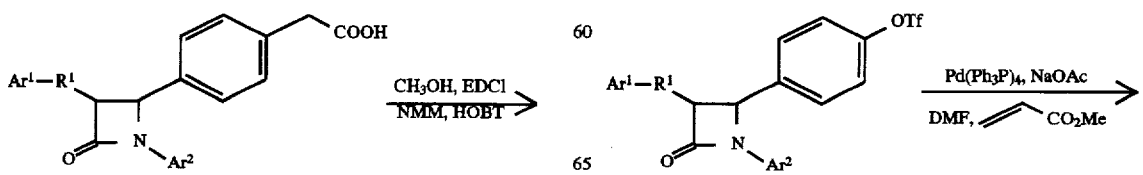
6
-continued
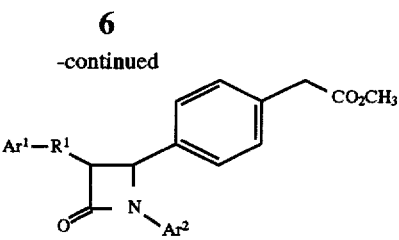
Method D:
Method E:
Method F:

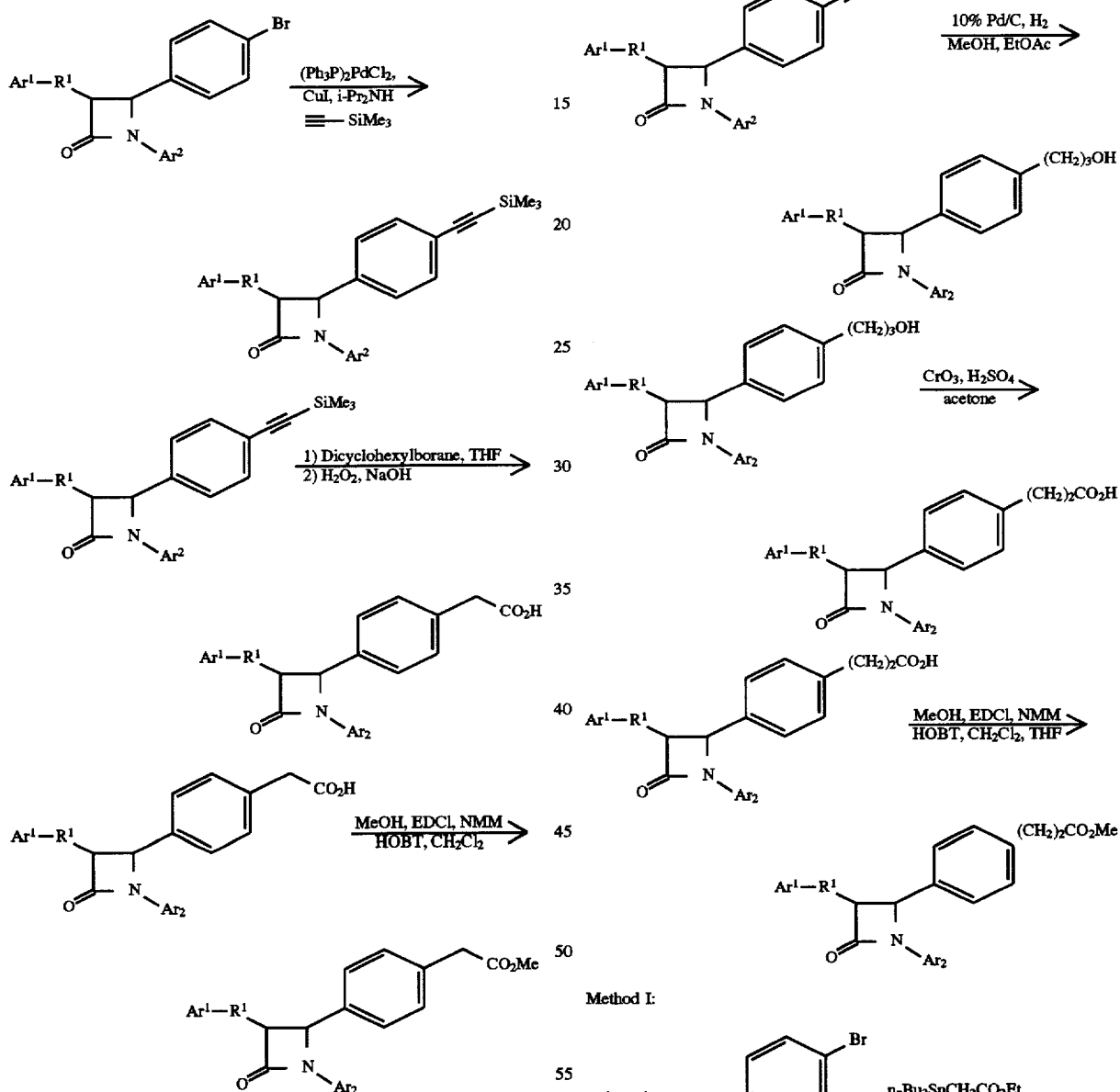
Method G:
Method H:
Method I:

Method J:

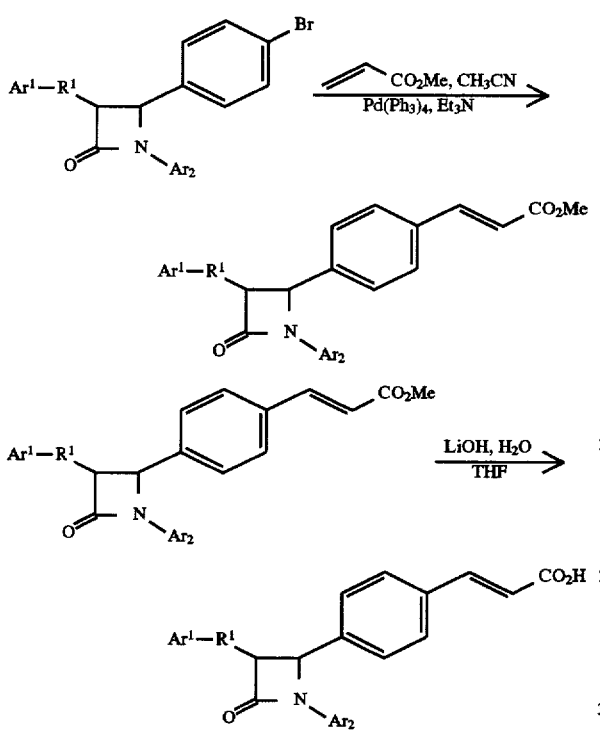

Method K:

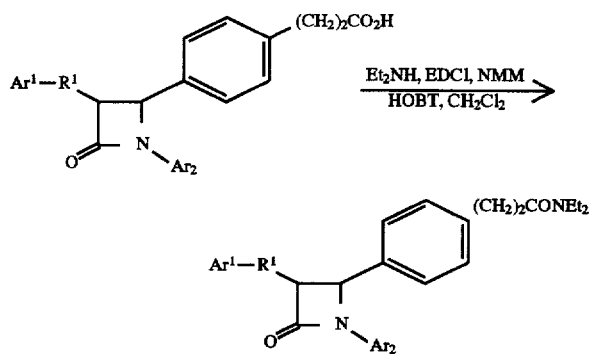

Starting compounds for the above reactions are all either commercially available or well known in the art and can be prepared via known methods.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| −COOH | −COOlalkyl, −COObenzyl, −COOphenyl |
| \>NH | \>NCOalkyl, \>NCObenzyl, \>NCOphenyl, |
| | \>NCH$_2$OCH$_2$CH$_2$Si(CH$_3$)$_3$, \>NC(O)OC(CH$_3$)$_3$, |
| | \>N−benzyl, \>NSi(CH$_3$)$_3$, \>NSi(CH$_3$)$_2$−C(CH$_3$)$_3$ |
| −NH$_2$ | −N(succinimide) |
| −OH | −OCH$_3$, −OCH$_2$OCH$_3$, −OSi(CH$_3$)$_2$−C(CH$_3$)$_3$, −OSi(CH$_3$)$_3$, or −OCH$_2$phenyl |

We have found that the compounds of this invention lower serum lipid levels, in particular serum cholesterol levels. Compounds of this invention have been found to inhibit the intestinal absorption of cholesterol and to significantly reduce the formation of liver cholesteryl esters in animal models. Thus, compounds of this invention are hypocholesterolemic agents by virtue of their ability to inhibit the intestinal absorption and/or esterification of cholesterol; they are, therefore, useful in the treatment and prevention of atherosclerosis in mammals, in particular in humans.

The in vivo activity of the compounds of formula I can be determined by the following procedure:

In Vivo Assay of Hypolipidemic Agents Using the Hyperlipodemic Hamster

Hamsters are separated into groups of six and given a controlled cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by intramuscular (IM) injection of ketamine and sacrificed by decapitation. Blood is collected into vacutainer tubes containing EDTA for plasma lipid analysis and the liver excised for tissue lipid analysis. Lipid analysis is conducted as per published procedures (Schnitzer-Polokoff, R., et al, Comp. Biochem. Physiol., 99A, 4 (1991), p. 665–670) and data is reported as percent reduction of lipid versus control.

The present invention also relates to a pharmaceutical composition comprising a compound of formula I and a pharmaceutically acceptable carrier. The compounds of formula I can be administered in any conventional dosage form, preferably an oral dosage form such as a capsule, tablet, powder, cachet, suspension or solution. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic dose of a compound of formula I is about 0.1 to about 30 mg/kg of body weight per day, preferably about 0.1 to about 15 mg/kg. For an average body weight of 70 kg, the dosage level is therefore from about 5 mg to about 1000 mg of drug per day, given in a single dose or 2–4 divided doses. The exact dose, however, is determined by the attending clinician and is dependent on the potency of the compound administered, the age, weight, condition and response of the patient.

For the combinations of this invention wherein the hydroxy substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day: for example, for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 2000 mg per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. Where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a substituted azetidinone cholesterol absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

Following are examples of preparing compounds of formula I. The stereochemistry listed is relative stereochemistry unless otherwise noted. The terms cis and trans refer to the relative orientations at the azetidinone 3- and 4-positions unless otherwise indicated.

EXAMPLE 1

Methyl 4-[1-(4-fluorophenyl)-4-oxo-3-(2-(4-fluorophenoxy)-ethyl)-2-azetidinyl]benzoate Reflux a solution of 4-formyl methylbenzoate (3.0 g, 18.3 mmol) and 4-fluoroaniline (2.0 g, 18.3 mmol) in toluene (200 mL) overnight with azeotropic removal of water via a Dean—Stark trap, monitoring conversion to the corresponding imine by $^1$H NMR of the crude mixture. Remove the Dean—Stark trap and add n-tributylamine (13.0 mL, 54.8 mmol). Add 4-fluorophenoxybutyryl chloride (27.4 mL, 27.4 mmol, 1M in toluene) slowly and reflux overnight, monitoring consumption of the imine by $^1$H NMR. Cool the mixture to room temperature, quench with 1M HCl and stir for ~30 min. Dilute the resulting solution with ethyl acetate (EtOAc), wash with 1M HCl, water and brine, dry over anhydrous $Na_2SO_4$ and concentrate to an amber oil. To reduce unreacted starting aldehyde, redissolve the oil in 50% $CH_3OH$/tetrahydrofuran (THF) (100 mL) and add $NaBH_4$ (1.22 g, 32 mmol). After gas evolution ceases (~15 min), quench the reaction with 1M HCl, dilute with EtOAc, wash with 1M HCl, water and brine, dry over anhydrous $Na_2SO_4$ and concentrate onto enough silica gel to obtain a free flowing powder. Load this powder onto a chromatography column prepacked with 20% EtOAc/hexanes and silica. Elute with 20% EtOAc/hexanes to obtain 2.48 g (31%) of the title compound as an 8/1 trans/cis mixture. Purify by HPLC (silica gel, 15% EtOAC/hexanes) to obtain pure cis and trans diasteromers.

In a similar manner, prepare the following compound:

1 A: Trans 1-(4-methoxyphenyl)-3-(3-phenylpropyl)-4-(4-bromophenyl)-2-azetidinone.

EXAMPLE 2

Trans Methyl 3-[4-[1-(4-Methoxyphenyl)-4-oxo-3-(3-phenylpropyl)-2-azetidinyl]phenyl]-2-propenoate Add $Pd(OAc)_2$ (0.036 g, 0.16 mol) and triphenylphosphine ($Ph_3P$) (0.097 g, 0.32 mmol) to anhydrous dimethylformamide (DMF) (3 mL) under $N_2$. Stir the mixture at room temperature until homogenous (5 min) and then add to a mixture of the product of Example 1A (3.6 g, 8.8 mmol), sodium acetate (0.72 g, 8.8 mmol), methyl acrylate (0.79 mL, 8.8 mmol) and DMF (10 ml) under $N_2$. Heat the resulting mixture to 130° C. overnight. Cool the reaction mixture to room temperature, and partion between ether and water. Wash the ether layer with water (5×) and brine, dry over $Na_2SO_4$ and concentrate to an oil. Chromatograph on silica gel (25% EtOAc/hexanes) to obtain 1.27 g (35%) of the title compound as a colorless oil. MS (EI): 455($M^+$, 17), 306(54), 215(45), 188(41), 149(100), 91(68).

EXAMPLE 3

Trans methyl 3-[4-[1-(4-methoxyphenyl)-4-oxo-3-(3-phenylpropyl)-2-azetidinyl]phenyl]-propanoate Dissolve the product of Example 2 (0.35 g, 0.77 mmol) in EtOAc (6 mL) and purge with $N_2$. Add 10% Pd/C (0.082 g), purge the resulting suspension with $H_2$ and stir under a balloon of $H_2$ for 3 h. Filter the mixture through celite, wash the filter cake with EtOAc and concentrate the filtrate to obtain 0.35 g (100%) of the title compound as a clear oil. MS (EI): 455($M^+$, 13), 308(31), 217(78), 185(25), 149(52), 129(100).

In a similiar manner, prepare:

3A: Trans methyl 3-[(3R, 2S)-4-[1-(4-methoxyphenyl)-4-oxo-3-(3-phenylpropyl)-2-azetidinyl]phenyl]propanoate: (prepared from trans methyl 3-[(3R, 2S)-4-[1-(4-methoxyphenyl)-4-oxo-3-(3-phenylpropyl)-2-azetidinyl] phenyl]-2-propenoate, prepared as described in Example 9. M.p. 91°–92° C. HRMS calc'd for $C_{29}H_{31}NO_4$: 457.2252; found 457.2274. (EI): 457($M^+$, 100), 308(52), 252(59), 160(46).

EXAMPLE 4

Trans Methyl 2-[4-[1-(4-Methoxyphenyl)-4-oxo-3 (R)-(3-phenylpropyl)-2(S)-azetidinyl]phenyl] ethanoate Step 1:(5S)-1-(5-Phenyl-1-oxo-pentanyl)-5-phenyloxalozidinone:

Slowly add 5-phenylvaleryl chloride (15.4 g, 78.1 mmol) in $CH_2Cl_2$ (40 mL) via cannula to a 0° C. solution of (5S)-5-phenyl-oxazolidinone (10.6 g, 65.1 mmol), triethylamine ($Et_3N$) (21.8 mL, 156.2 mmol) and dimethylaminopyridine (DMAP) (0.56 g, 4.56 mmol) in $CH_2Cl_2$ (160 mL). After addition, allow the mixture to warm to room temperature overnight. Add water and stir the mixture for 30 min.; wash with 1M HCl, water, $NaHCO_3$ (sat'd), water and brine, dry over anhydrous $Na_2SO_4$ and concentrate to obtain the title compound of Step 1 as an amber oil, 24.2 g (~100%).

Step 2:

Add $TiCl_4$ (38 mL, 38 mmol, 1M in $CH_2Cl_2$) dropwise to a −40° C. solution of (5S)-1-(5-phenyl-1-oxo-pentanyl)-5-phenyl-oxalozidinone (12.3 g, 38.0 mmol) in $CH_2Cl_2$ (125 mL) over 10 min. Stir for an additional 10 min., then add Hunig's base (13.2 mL, 76 mmol) over 8 min. while maintaining the temperature at −40° C. Stir the resulting solution for 30 min. Add N-(4-benzyloxybenzylidene)-4-methoxyaniline (21.6 g, 68.2 mmol) in $CH_2Cl_2$ (450 mL) via cannula over 40 min., again maintaining the reaction temperature at −50° to −40° C. Stir the mixture for 3 h and allow to warm to −20° C. Quench the reaction by slowly adding acetic acid (20 ml) in $CH_2Cl_2$ (100 mL), stir the mixture for 30 min. and then pour into a 0° C. solution of 2N $H_2SO_4$ (500 mL) and EtOAc (500 mL) and stir rapidly for 1 h. Filter the resulting mixture, extract the filtrate with EtOAc, wash the combined extracts with $NaHCO_3$ (sat'd) and brine, dry over $Na_2SO_4$ and concentrate to a beige solid (20 g). Recrystallize from EtOAc to obtain 8.08 g (34%) of an off white solid.

Step 3: Trans (3R,4S)- 1-(-methoxyphenyl)-3-(3-phenylpropyl)-4-(4-benxyloxyphenyl)-2-azetidinone:

Add N,O-bis(trimethylsilyl)acetamide (4.6 ml, 18.8 mmol) to a 90° C. solution of the product of Step 2 (8.03 g, 12.5 mmol) in toluene (100 mL) and stir for 1 h. Add tetrabutylammonium fluoride (0.16 g, 0.63 mmol) and stir the mixture at 90° C. for an additional hour. Cool the mixture to room temperature and quench the reaction with $CH_3OH$ (10 mL). Dilute the mixture with EtOAc, wash with 1M HCl, $NaHCO_3$ (sat'd), water and brine, then concentrate to a white solid. Purify the solid further by chromatography on silica gel (30% EtOAC/hexane) to obtain 5.46 g (91%) of the title compound of Step 3 as a white solid.

Step 4: Trans(3R,4S)-1-(-methoxyphenyl)-3-(3-phenylpropyl)-4-(4-hydroxyphenyl)-2-azetidinone:

Hydrogenate a suspension of the product of Step 3 in 50% $CH_3OH$/EtOAc (100 mL) with 10% Pd/C (0.42 g) on a Parr aparatus at 60 psi overnight. Filter the reaction mixture through celite and concentrate the filtrate to provide 5 g of a foam. Purify the foam by silica gel chromatography (40–100% EtOAc/hexane) to provide 4.05 g (92%) of the title compound of Step 4 as a white solid.

Step 5: Trans (3R,4S)-1-(-methoxyphenyl)-3-(3-phenylpropyl)-4-(4-trifluoromethanesulfonyl)phenyl)-2-azetidinone:

Add triflilic anhydride (0.57 mL, 3.4 mmol) to a 0° C. solution of the product of Step 4 (1.2 g, 3.1 mmol), DMAP (0.1 g) and 2,4,6-collidine (0.44 mL, 3.4 mmol) in $CH_2Cl_2$ (15 mL). After 30 min., quench the reaction with water and extract with EtOAc. Combine the extracts, wash with $NH_4Cl$ (sat'd), $NaHCO_3$ (sat'd), water and brine, dry over $Na_2SO_4$ and concentrate to obtain 1.7 g (100%) of the title compound of Step 5 as an oil.

Step 6: Trans (3R,4S)-1-(4-Methoxyphenyl)-3-(3-phenylpropyl)-4-(4-vinylphenyl)-2-azetidinone:

Dissolve the product of Step 5 (1.22g, 2.35 mmol) in dioxane (30 mL), add LiCl (0.30 g, 7.04 mmol) and palladium tetrakistriphenylphosphine ($Pd(Ph_3P)_4$) (0.28 g, 0.24 mmol). Add vinyltributyltin (0.83 ml, 2.82 mmol) and heat the mixture to 90° C., monitoring the reaction by TLC (25% EtOAc/hexanes). Cool the mixture to room temp., treat with 2.5M KF (30 mL) and stir the mixture overnight. Filter the resulting solution, dilute with EtOAc, wash with water and brine, dry over $Na_2SO_4$ and concentrate to a yellow oil. Chromatograph on silica gel (20% EtOAc/hexane) to obtain 0.447 g (50%) of the title compound of Step 6 as an oil.

Step 7: Trans Methyl 4-[1-(4-Methoxyphenyl)-4-oxo-3(R)-(3-phenylpropyl)-2(S)-azetidinyl]phenyl-2-ethanol:

Add borane tetrahydrofuran complex (3.4 mL, 3.4 mmol) to a 0° C. solution of the product of Step 6 (0.45 g, 1.12 mmol) in THF (15 mL) and allow the mixture to warm to room temperature overnight. Add 2N NaOH (1.7 ml) followed by 30% $H_2O_2$ (1.2 mL) and stir the mixture for 3 h. Quench the mixture by adding 0.8M $Na_2SO_3$ solution (2 mL). Extract the mixture ether, wash the etheral extracts with water and brine, dry over $Na_2SO_4$ and concetrate. Chromatograph on silica (30% EtOAc/hexanes) to obtain 0.18 g (41%) of the title compound of Step 7 as an oil.

Step 8: Trans Methyl 2-[4-[1-(4-Methoxyphenyl)-4-oxo-3 (R)-(3-phenylpropyl)-2(S)-azetidinyl]phenyl]-acetic acid:

Add Jones Reagent (0.4 ml, prepared by dissolving 6.7 g chromic acid in concentrated $H_2SO_4$ and diluting with distilled water to 50 mL) to a solution of the product of Step 7 (0.15 g, 0.36 mmol) in acetone (4 mL), monitoring the reaction by TLC (5% MeOH/$CH_2Cl_2$). Add $CH_3OH$ (2 mL) and stir the mixture for 30 min. Concentrate the mixture, partition the residue between water and $CH_2Cl_2$, and extract with $CH_2Cl_2$. Combine the extracts, wash with $Na_2SO_3$ (sat'd), water and brine, dry over $Na_2SO_4$ and concentrate to obtain 0.144 g (93%) of the title compound of Step 8 as a yellow foam.

Step 9:

Using a well known procedure, add 1-(3-dimethylaminopropyl)-3-ethylcarbodiimide hydrochloride (EDCl) to a solution of the product of Step 8, ethanol, hydroxybenzotriazole (HOBT) and N-methylmorpholine (NMM) in $CH_2Cl_2$ and stir the mixture overnight. Dilute the resulting reaction mixture with $CH_2Cl_2$, wash with 1M HCl, water and brine, dry over an hydrous $Na_2SO_4$ and concentrate to an oil. Chromatograph the residue on silica (3% $CH_3OH$/$CH_2Cl_2$) to obtain 0.090 g (61%) of the title compound. HRMS calc'd for $C_{28}H_{29}NO_4$: 443.2097; found 443.2093. MS (CI): 444 ($M^{+1}$,100).

EXAMPLE 5

Trans methyl 3-[3-benzyloxy-4-[1-(4-fluorophenyl)-4-oxo-3-(3-phenylpropyl)-2-azetidinyl]phenyl] propenoate Combine trans-1-(-fluorophenyl)-3-(3-phenylpropyl)-4-(4-bromo-2-benxyloxyphenyl)-2-azetidinone (0.55 g, 1.0 mmol) (prepared according to the procedure of Example 1 ), triethylamine (0.28 mL, 2.0 mmol), methyl acrylate (0.18 mL, 2.0 mmol) and $Pd(Ph_3P)_4$ (0.058 g, 0.05 mmol) in $CH_3CN$ (2 mL) and heat to 80° C. over night. Monitor the reaction by TLC (25% EtOAC/hexane); add methyl acrylate (0.18 mL, 2.0 mmol) and Pd(Ph$_3$P)$_4$ (0.058 g, 0.05 mmol) and heat the mixture for an additional 20 h. at 80° C. Cool the reaction mixture to room temperature, dilute with EtOAc, wash with 0.1N HCl, water and brine, dry over Na$_2$SO$_4$ and concentrate. Chromatograph the residue on silica (20% EtOAc/hexane) to obtain 0.27 g (48%) of the title compound as a yellow solid.

5A: In a similar manner, prepare trans methyl 3-[4-[1-(4-fluorophenyl)-4-oxo-3-(3-phenylpropyl)-2-azetidinyl]phenyl]propenoate.

EXAMPLE 6 trans methyl 3-[3-hydroxy-4-[1-(4-fluorophenyl)-4-oxo-3-(3-phenylpropyl)-2-azetidinyl]phenyl]propionate Dissolve the product of Example 5 (0.266 g, 0.48 mmol) in EtOAc (16 mL), dilute with CH$_3$OH (20 mL) and purge with N$_2$. Add 20% Pd/C (0.05 g), purge the mixture with H$_2$ and then stir under a balloon of H$_2$ overnight. Filter the reaction mixture through celite. Wash the filter cake with EtOAc and concentrate the filtrate to give 0.156 g of the title compound as a colorless oil. HRMS calc'd for C$_{28}$H$_{28}$NO$_4$:M+H 462.2081; found 462.2070.MS (CI): 462 (M$^{+1}$,37), 351 (17), 293(41 ), 138(100).

EXAMPLE 7 trans 3-[3-hydroxy-4-[1-(4-fluorophenyl)-4-oxo-3-(3-phenylpropyl)-2-azetidinyl]phenyl]propionic Acid Dissolve the product of Example 6 (0.066 g, 0.14 mmol) in THF (3 mL), add LiOH (0.04 g, 0.86 mmol) and stir the mixture at room temperature overnight. Acidify the solution to pH 3 with 1M HCl, dilute with EtOAc, wash with water and brine, dry over Na$_2$SO$_4$ and concentrate to give 0.061 g, (91%) of the title compound as an oil. HRMS calc'd for C$_{27}$H$_{26}$NO$_4$F: M+H 448.1924; found 448.1911. (FAB): 444 (M$^{+1}$,100).

EXAMPLE 8

Trans Methyl 3-[3-[1-phenyl-4-oxo-3-(3-phenylpropyl)-2-azetidinyl]phenyl]propanoate Step 1: Prepare trans 1-phenyl-3-(3-phenylpropyl)-4-(3-benzyloxyphenyl)-2-azetidinone in a manner similar to that described in Example 1.

Step 2: Using the procedure of Example 4, Step 4, treat the product of Step 1 to obtain trans 1-phenyl-3-(3-phenylpropyl)-4-(3-hydroxyphenyl)-2-azetidinone.

Step 3: Using the procedure of Example 4, Step 5, treat the product of Step 2 to obtain trans 1-phenyl-3-(3-phenylpropyl)-4-((3-trifluoromethylsulfonyl))phenyl)-2-azetidinone.

Step 4: Using the procedure of Example 5, treat the product of Step 3 to obtain compound 8-1, trans methyl 3-[3-[1-phenyl-4-oxo-3-(3-phenylpropyl)-2-azetidinyl]phenyl]-2-propenoate.

Step 5: Using the procedure of Example 3, treat the product of Step 4 to obtain the title compound (8-2). HRMS calc'd for C$_{28}$H$_{29}$NO$_3$: M+H 428.2226; found 428.2235.MS (CI): 428 (M$^{+1}$,100).

EXAMPLE 9

Trans (3R,2S)-Methyl 3-[4-[1-(4-methoxyphenyl)-4-oxo-3-(3-phenylpropyl)-2-azetidinyl]phenyl]-2-propenoate Heat the product of Example 4, Step 5 (0.51 g, 0.98 mmol), sodium acetate (0.1 g, 1.1 mmol), DMF (6 mL) and methyl acrylate (0.1 mL, 1.1 mmol) to 130° C. Add Pd(Ph$_3$P)$_4$ (0.1 g, 0.11 mmol) and stir the mixture at 130° C. overnight. Cool the mixture to room temperature, partition between water and ether, and extract with ether. Combine the etheral extracts, wash with water and brine, dry over Na$_2$SO$_4$ and concentrate. Chromatograph the residue on silica (25% EtOAc/hexanes) to provide 0.18 g (40%) of the title compound as a clear oil. HRMS calc'd for C$_{29}$H$_{29}$NO$_4$: 455.2097; found 455.2080.MS (EI): 455 (M$^+$,72), 371(40), 306(56), 252(100).

EXAMPLE 10

(3S, 2R) trans methyl 4-[1-(4-chlorophenyl)-4-oxo-3-(2-(4-fluorophenoxy)ethyl)-2-azetidinyl]phenyl-2-propenoate (10A) and (3R, 2S) trans methyl 4-[1-(4-chlorophenyl)-4-oxo-3-(2-(4-fluorophenoxy)ethyl)-2-azetidinyl]phenyl-2-propenoate (10B)

Add 4-(4-fluorophenoxy)butyryl chloride (0.72 g, 3.34 mmol) dropwise to a solution of 4-formyl methylpropenoate 4-chloroaniline imine (0.5 g, 1.67 mmol) and Hunig's base (0.87 mL, 5.0 mmol) in dichloroethane (46 mL) at 80° C. Reflux the mixture overnight, cool to room temperature, quench with 1M HCl and stir for 15 min. Wash the mixture with NaHCO$_3$ (sat'd), water and brine, dry over Na$_2$SO$_4$ and concentrate. Chromatograph the residue on silica (40% EtOAc/hexane). To remove 4-formyl methylbenzoate contaminant, dissolve the product in 50% CH$_3$OH/THF and treat with NaBH$_4$ (1.5 g). After 30 min, quench with NH$_4$Cl (sat'd), wash with NH$_4$Cl (sat'd), water and brine, dry over Na$_2$SO$_4$ and concentrate. Chromatograph the residue on silica (35% EtOAc/hexanes) to provide 0.57 g (33%) of trans methyl 4-[1-(4-chlorophenyl)-4-oxo-3-(2-(4-fluorophenoxy)ethyl)-2-azetidinyl]phenyl-2-propenoate. Resolve the diasteromers by chiral HPLC (Chiracel AS column, 30% isopropanol/hexanes, 70 mL/min) to give 0.128 g compound 10A and 0.139 g compound 10B.

10A: HRMS calc'd for C$_{27}$H$_{23}$NO$_4$Cl: 480.1378; found 480.1378. (CI): 480(M$^+$, 100), 215(99).

10B: HRMS calc'd for C$_{27}$H$_{23}$NO$_4$Cl: 480.1378; found 480.1369. (CI): 480(M$^+$, 88), 215(100).

EXAMPLE 11

Trans 3-[4-[1-(4-Methoxyphenyl)-4-oxo-3-(3-phenylpropyl)-2-azetidinyl]phenyl]propanoic acid Step 1: Hydrolyze the product of Example 2 according to the procedure described in Example 7 to obtain trans 3-[4-[1-(4-methoxyphenyl)-4-oxo-3-(3-phenylpropyl)-2-azetidinyl]phenyl]-2-propenoic acid (compound 11-1 ).

Step 2: Hydrogenate the product of Step 1 according to the procedure described in Example 3 to obtain the title compound (11-2). HRMS calc'd for C$_{28}$H$_{31}$NO$_4$:M+H 444.2175; found 444.2165. (FAB): 444(M$^{+1}$,100).

EXAMPLE 12

Trans Methyl (3R, 2S)-4-[1-(4-fluorophenyl)-4-oxo-3-(3-phenylpropyl)-2-azetidinyl]benzene Acetate Step 1: Trans (3R, 4S)-1-(4-fluorophenyl)-4-(4-((trimethylsilyl)acetylenyl)phenyl)-3-(3-phenylpropyl)-2-azetidinone:

Heat a mixture of trans (3R, 4S)-1-(4-fluorephenyl)-4-(4-bromophenyl)-3-(3-phenylpropyl)-2-azetidinone (0.69 g, 1.57 mmol) (prepared from N-(4-bromobenzylidene)-4-fluoroaniline and (5S)-1-(5-phenyl-1-oxopentanyl)-5-phenyloxazolidinone using the procedure described in steps 2 and 3 of Example 4), (trimethylsilyl)acetylene (0.33 mL, 2.36 mmol), bis(triphenylphosphine)palladium (11) chloride ((Ph$_3$P)$_2$PdCl$_2$) (0.055 g, 0.079 mmol) and diisopropylamine (6 mL) to 80° C. Monitor the reaction by TLC. After 80 min, add additional (trimethylsilyl)acetylene (0.33 mL, 2.36 mmol). After an additional 50 min, cool the mixture to room temperature, filter through celite and wash the filter cake with CH$_2$Cl$_2$. Concentrate the filtrate onto enough silica so that a free flowing powder is obtained. Load the resulting powder onto a chromatography column prepacked with silica and 10% EtOAc/hexane. Elute with 10% EtOAc/hexane to obtain 0.595 g (83%) of the title compound of Step 1 as a light brown solid. MS(FAB): 456 (M$^+$, 100), 318(37), 296(35).

Step 2: Trans (3R, 2S)-4-[1-(4-fluorophenyl)-4-oxo-3-(3-phenylpropyl)-2-azetidinyl]benzeneacetic acid:

Add cyclohexane (1.08 mL, 10.64 mmol) to a 0° C. solution of borane (5.3 mL, 5.3 mmol, 1M in THF). Stir at 0° C. for 1 h. Dropwise add the product of step 1 (0.485 g, 1.07 mmol) in THF (7.5 mL) and keep the mixture at 0° C. overnight (22 h). Sequentially add CH$_3$OH (0.43 mL), 3N NaOH (1.06 mL) and 30 % H$_2$O$_2$ (1.2 mL) to the 0° C. mixture. Allow the mixture to warm to room temperature and stir for 3 h. Pour the mixture into brine and acidify with 1M HCl. Extract with EtOAc, combine the extracts, wash with water and brine, dry over anhydrous Na$_2$SO$_4$ and concentrate onto enough silica that a free flowing powder is obtained. Load the resulting powder onto a chromatography column prepacked with silica and 5% CH$_3$OH/CH$_2$Cl$_2$. Elute with 5% CH$_3$OH/CH$_2$Cl$_2$ to obtain the title compound of Step 2, 0.227 g (52%). HRMS calc'd for C$_{26}$H$_{25}$NO$_3$F: (M+H) 418.1818; found 418.1820. MS(CI): 418 (M+H, 18), 235(29), 145(55), 83(100).

Step 3: Using a procedure similar to that of Example 4, step 9, treat the product of step 3 to obtain the title compound, 0.023 g (25%). HRMS calc'd for C$_{28}$H$_{29}$NO$_3$F: (M+H) 446.2131; found 446.2150.MS(CI): 446 (M+H, 100), 277(13), 138(44).

EXAMPLE 13

Trans Methyl (3R, 2S)-4-[1-(4-fluorophenyl)-4-oxo-3-(3-phenylpropyl)-2-azetidinyl]benzenepropanoate Step 1: Trans (3R, 4S)-1-(4-fluorophenyl)-4-(4-(3-hydroxy-1-propynyl)phenyl)-3-(3-phenylpropyl)-2-azetidinone:

Use a procedure similar to that of Example 12, Step 1, substituting propargyl alcohol (0.20 mL, 3.49 mmol) for (trimethylsilyl)acetylene and refluxing overnight. Filter and chromatograph as in Example 12, Step 1, using a column prepacked with silica and 30% EtOAc/hexane. Elute with 30% EtOAc/hexane to obtain the title compound of Step 1, 0.73g (75%), as a yellow oil. HRMS calc'd for C$_{27}$H$_{25}$NO$_2$F: (M+H) 414.1869; found 414.1854.MS(CI): 414 (M+H, 72), 259(32), 138(100).

Step 2: Trans (3R, 4S)-1-(4-fluorophenyl)-4-(4-(3-hydroxy-1-propyl)phenyl)-3-(3-phenylpropyl)-2-azetidinone:

Using the procedure of Example 6, treat the product of Step 1 to obtain 0.42 g (100%) of the title compound of Step 2. MS(CI): 418 (M+H, 100), 138(55).

Step 3: Trans (3R, 2S)-4-[1-(4-fluorophenyl)-4-oxo-3-(3-phenylpropyl)-2-azetidinyl]benzenepropanoic acid:

Add Jone's Reagent (1.0 mL, prepared as described in Example 4, step 7) to a 0° C. solution of the product of Step 2 in acetone (8 mL). Monitor the reaction by TLC (5% CH$_3$OH/CH$_2$Cl$_2$). Upon consumption of starting material, quench the reaction by the addition of CH$_3$OH and concentrate in vacuo. Dissolve the residue in water, and adjust to pH 13 with NaOH. Extract the resulting solution with ether, acidify the aqueous layer to pH 3 with HCl (conc.) and extract with EtOAc. Combine the extracts, wash with 10% NaHSO$_3$, water and brine, dry over anhydrous Na$_2$SO$_4$ and concentrate onto enough silica that a free flowing powder is obtained. Load the resulting powder onto a chromatography column prepacked with silica and 5% CH$_3$OH/CH$_2$Cl$_2$. Elute with 5-8% CH$_3$OH/CH$_2$Cl$_2$ to obtain 0.243 g (53%) of the title compound of Step 3 as a white foam. HRMS calc'd for C$_{27}$H$_{27}$NO$_3$F:(M+H) 432.1975; found 432.1972. MS(CI): 432 (M+H, 100).

Step 4: Using a procedure similar to that of Example 4, step 9, but using THF, treat the product of step 3 to obtain the title compound, 0.54 g (57%). HRMS calc'd for C$_{28}$H$_{29}$NO$_3$F: (M+H) 446.2131; found 446.2150. MS(CI): 446 (M+H, 100), 277(13), 138(44).

EXAMPLE 14

Trans Ethyl (3R,2S)-4-[1-(4-fluorophenyl)-4-oxo-3-(3-phenylpropyl)-2-azetidinyl]benzene acetate Dry ZnBr$_2$ (0.335 g, 1.49 mmol) at 130° C. under vacuum overnight, then cool to room temperature under nitrogen. Add a solution of trans (3R, 4S)-1-(4-fluorophenyl)-4-(4-bromophenyl)-3-(3-phenylpropyl)-2-azetidinone (0.0.50 g, 1.14 mmol) and ethyl 2-tributyltin acetate (0.56 g, 1.49 mmol) in DMF (3 mL) via cannula under nitrogen. Heat the mixture to 80° C. Monitor consumption of starting material by TLC (15% EtOAc/hexane) and upon completion, cool to room temperature, filter through celite, and wash the filter cake with EtOAc. Add 2.5M KF (10 mL) to the filtrate, stir for 3h, dilute with EtOAc, wash with water and brine, dry over anhydrous Na$_2$SO$_4$ and concentrate onto enough silica that a free flowing powder is obtained. Load the resulting powder is loaded onto a chromatography column prepacked with silica and 15% EtOAc/hexane. Elute with 15% EtOAc/hexane to obtain the title compound as a yellow oil, 0.416 g (82%). HRMS calc'd for C$_{28}$H$_{29}$NO$_3$F: (M+H) 446.2131; found 446.2123. MS(FAB): 446 (M+H, 100), 308(18), 286 (24).

EXAMPLE 15

Trans (3R, 2S)-3-[4-[1-(4-Fluorophenyl)-4-oxo-3-(3-phenylpropyl)-2-azetidinyl]phenyl]-E-2-propenoic Acid Step 1: Trans methyl (3R, 2S)-3-[4-[1-(4-fluorophenyl)-4-oxo-3-(3-phenylpropyl)-2-azetidinyl]phenyl]-E-2-propenoate:

Treat trans (3R, 4S)-1-(4-fluorophenyl)-4-(4-bromophenyl)-3-(3-phenylpropyl)-2-azetidinone methyl acrylate in a manner similar to that described in Example 5 to obtain the title compound of Step 1. HRMS calc'd for C$_{28}$H$_{27}$NO$_3$F: (M+H) 444.1975; found 444.1971. MS(CI): 444 (M+H, 100).

Step 2: Treat the, product of step 1 as described in Example 7, purifying by chromatography on a column prepacked with silica and 0.5% HOAc/2.5% EtOH/97% CH$_2$Cl$_2$, eluting with the same eluant to obtain the title compound. HRMS calc'd for C$_{27}$H$_{25}$NO$_3$F: (M+H) 430.1818; found 430.1810.MS(CI): 430 (M+H, 100), 293(26), 177(74), 138(52).

EXAMPLE 16

Trans N,N-Diethyl-(3R, 2S)-4-[1-(4-fluorophenyl)-4-oxo-3-(3-phenylpropyl)-2-azetidinyl]benzenepropanamide Add EDCl (0.058 g, 0.303 mmol) to a mixture of the product 5 of Step 3 of Example 13 (0.092 g, 0.213 mmol), HOBT hydrate (0.035 g, 0.256 mmol), NMM (0.029 mL, 0.277 mmol) and Et$_2$N (0.044 mL, 0.427 mmol) in CH$_2$Cl$_2$ (2.5 mL). Stir the resulting mixture overnight until TLC (50% EtOAc/hexane) indicates consumption of starting material. Dilute the mixture with CH$_2$Cl$_2$, wash with 0.2N HCl, water and brine, dry over anhydrous Na$_2$SO$_4$ and concentrate onto enough silica such that a free flowing powder is obtained. Load the resulting powder is loaded onto a chromatography column prepacked with silica and 35% EtOAc/hexane. Elute with 35–50% EtOAc/hexane to obtain an oil which is further purified by silica chromatography, eluting with 35–50% EtOAc/hexanes to obtain the title compound, 0.68 g (73%), as an oil. MS(Cl): 487 (M+, 100), 350(19), 318(37). HRMS(FAB): calcd. for C$_{31}$H$_{36}$N$_2$O$_2$F(M$^+$1), 487.2761; found 487.2783.

The following formulations exemplify some of the dosage forms of this invention. In each the term "active compound" designates a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10–15 minutes. Granulate the mixture with Item No. 3.Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | Total | 250 | 700 |

Method of Manufacture

Mix Item Nos. 1,2 and 3 in a suitable blender for 10–15 minutes. Add Item No. 4 and mix for 1–3 minutes. Fill the mixture into suitable two-piece hard gelatin capsules on a suitable encapsulating machine.

Representative formulations comprising a cholesterol biosynthesis inhibitor are well known in the art. It is contemplated that where the two active ingredients are administered as a single composition, the dosage forms disclosed above for substituted azetidinone compounds may readily be modified using the knowledge of one skilled in the art.

Using the test procedures described above, the following in vivo data were obtained for exemplified compounds. Data is reported as 15 percent change (i.e., % reduction in cholesterol esters) versus control, therefore, negative numbers indicate a positive lipid-lowering effect.

| Ex. # | % Reduction Serum Cholest. | Cholest. Esters | Dose mg/kg |
|---|---|---|---|
| 1 (trans) | −28 | −76 | 50 |
| 1 (cis) | −17 | 0 | 50 |
| 2 | −38 | −90 | 50 |
| 3 | −41 | −93 | 50 |
| 3A | −20 | −76 | 3 |
| 4 | −49 | −96 | 10 |
| 5A | −21 | −48 | 10 |
| 8-2 | 0 | −29 | 10 |
| 9 | −19 | −75 | 10 |
| 10A | 0 | −12 | 10 |
| 10B | 0 | −21 | 10 |
| 11-2 | −19 | −64 | 10 |
| 12 | −44 | −97 | 10 |
| 12A | −16 | −61 | 5 |
| 13 | −32 | −63 | 10 |
| 13A | −26 | −72 | 10 |
| 14 | −15 | −29 | 1 |
| 15 | 0 | −50 | 10 |
| 16 | 0 | −19 | 10 |

We claim:

1. A compound represented by the formula

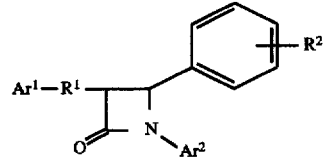

or a pharmaceutically acceptable salt thereof, wherein:
Ar$^1$ is phenyl or R$^3$-substituted phenyl;
Ar$^2$ is phenyl or R$^4$-substituted phenyl;
R$^1$ is selected from the group consisting of
—(CH$_2$)$_q$—, wherein q is 2 or 3;
—(CH$_2$)$_e$—Z—(CH$_2$)$_r$, wherein Z is is —O—, e is 0 and r is 2;
R$^2$ is —(lower alkylene)—COR$^5$ or —(CH═CH)—COR$^5$;
R$^3$ and R$^4$ are independently selected from the group consisting of 1–3substituents independently selected from the group consisting of —OR$^6$ and halogen;
R$^5$ is —OR or —NRR$^{12}$, wherein R and R$^{12}$ are independently selected from the group consisting of hydrogen and lower alkyl; and
R$^6$ are independently selected from the group consisting of hydrogen and lower alkyl.

2. A compound of claim 1 selected from the group consisting of trans methyl 3-[4-[1-(4-methoxyphenyl)-4-oxo-3-(3-phenylpropyl)-2-azetidinyl]phenyl]-2-propenoate;

trans methyl 4-[1-(4-methoxyphenyl)-4-oxo-3-(3-phenylpropyl)-2-azetidinyl]benzenepropanoate;

trans methyl (3S, 2R)-4-[1-(4-methoxyphenyl)-4-oxo-3-(3-phenylpropyl)-2-azetidinyl]benzenepropanoate;

trans methyl 4-[1-(4-methoxyphenyl)-4-oxo-3-(3-phenylpropyl)-2-azetidinyl]benzeneacetate;

trans methyl 3-[1-phenyl-4-oxo-3-(3-phenylpropyl)-2-azetidinyl]benzenepropanoate;

trans (3R,4S)-methyl 3-[4-[1-(4-methoxyphenyl)-4-oxo-3-(3-phenylpropyl)-2-azetidinyl]phenyl]-2-propenoate;

(3S, 2R) trans methyl 3-[4-[1-(4-chlorophenyl)-4-oxo-3-(2-(4-fluorophenoxy)ethyl)-2-azetidinyl]phenyl]-2-propenoate;

(3R, 2S) trans methyl 3-[4-[1-(4-chlorophenyl)-4-oxo-3-(2-(4-fluorophenoxy)ethyl)-2-azetidinyl]phenyl]-2-propenoate;

trans 4-[1-(4-methoxyphenyl)-4-oxo-3-(3-phenylpropyl)-2-azetidinyl]benzenepropanoic acid;

trans methyl 3-[4-[1-(4-fluorophenyl)-4-oxo-3-(3-phenylpropyl)-2-azetidinyl]phenyl]propenoate;

trans (3R, 2S)-4-[1-(4-fluorophenyl)-4-oxo-3-(3-phenylpropyl)-2-azetidinyl]benzeneacetic acid;

trans methyl (3R, 2S)-4-[1-(4-fluorophenyl)-4-oxo-3-(3-phenylpropyl)-2-azetidinyl]benzene acetate;

trans (3R, 2S)-4-[1-(4-fluorophenyl)-4-oxo-3-(3-phenylpropyl)-2-azetidinyl]benzenepropanoic acid;

trans methyl (3R, 2S)-4-[1-(4-fluorophenyl)-4-oxo-3-(3-phenylpropyl)-2-azetidinyl]benzenepropanoate;

trans ethyl (3R, 2S)-4-[1-(4-fluorophenyl)-4-oxo-3-(3-phenylpropyl)-2-azetidinyl]benzene acetate;

trans (3R, 2S)-3-[4-[1-(4-fluorophenyl)-4-oxo-3-(3-phenylpropyl)-2-azetidinyl]phenyl]-E-2-propenoic acid; and trans N,N-diethyl-(3R, 2S)-4-[1-(4-fluorophenyl)-4-oxo-3-(3-phenylpropyl)-2-azetidinyl]benzenepropanamide.

3. A method of lowering serum cholesterol levels in a mammal in need of such treatment comprising administering an effective amount of a compound of claim 1.

4. A pharmaceutical composition comprising a cholesterol-lowering effective amount of a compound of claim 1 in a pharmaceutically acceptable carrier.

5. A compound of claim 1 wherein R is lower alkyl.

6. A compound of claim 1 wherein $R^2$ is —(ethylene)—COOR.

* * * * *